United States Patent
Jang et al.

(10) Patent No.: US 10,067,266 B2
(45) Date of Patent: Sep. 4, 2018

(54) METHOD OF PRODUCING RESIN FOR THIOURETHANE-BASED OPTICAL MATERIAL USING GENERAL-PURPOSE POLYISOCYANATE COMPOUND, RESIN COMPOSITION FOR THIOURETHANE-BASED OPTICAL MATERIAL AND THIOURETHANE-BASED OPTICAL MATERIAL INCLUDING RESIN PRODUCED BY THE METHOD

(75) Inventors: Dong Gyu Jang, Daejeon (KR); Soo Gyun Roh, Daejeon (KR); Jong Hyo Kim, Daejeon (KR)

(73) Assignee: KOC SOLUTION CO., LTD., Yuseong-Gu, Daejeon (KR)

( * ) Notice: Subject to any disclaimer, the term of this patent is extended or adjusted under 35 U.S.C. 154(b) by 58 days.

(21) Appl. No.: 14/002,389

(22) PCT Filed: Mar. 2, 2012

(86) PCT No.: PCT/KR2012/001590
§ 371 (c)(1),
(2), (4) Date: Oct. 1, 2013

(87) PCT Pub. No.: WO2012/118351
PCT Pub. Date: Sep. 7, 2012

(65) Prior Publication Data
US 2014/0039145 A1  Feb. 6, 2014

(30) Foreign Application Priority Data
Mar. 2, 2011  (KR) .................. 10-2011-0018673

(51) Int. Cl.
| | |
|---|---|
| G02B 1/04 | (2006.01) |
| C08G 18/72 | (2006.01) |
| C08G 18/73 | (2006.01) |
| C08G 18/75 | (2006.01) |
| C08G 18/38 | (2006.01) |
| C07C 319/14 | (2006.01) |
| C08K 5/00 | (2006.01) |

(52) U.S. Cl.
CPC .............. *G02B 1/04* (2013.01); *C07C 319/14* (2013.01); *C08G 18/3868* (2013.01); *C08G 18/722* (2013.01); *C08G 18/73* (2013.01); *C08G 18/755* (2013.01); *C08K 5/005* (2013.01)

(58) Field of Classification Search
None
See application file for complete search history.

(56) References Cited

U.S. PATENT DOCUMENTS

| | | | | |
|---|---|---|---|---|
| 2,831,896 A | * | 4/1958 | Holly | .................... C07C 323/00 528/374 |
| 3,402,155 A | * | 9/1968 | Kutch | ............................ 528/374 |
| 3,472,913 A | * | 10/1969 | Ephraim | ........................ 528/374 |
| 5,191,055 A | † | 3/1993 | Kanemura | |
| 5,608,115 A | * | 3/1997 | Okazaki | ................ C07C 321/14 568/61 |
| 7,872,093 B2 | | 1/2011 | Kousaka | |
| 2004/0096666 A1 | * | 5/2004 | Knox | ...................... B32B 27/08 428/412 |
| 2007/0058253 A1 | * | 3/2007 | Aiiso et al. | .................... 359/487 |
| 2009/0259001 A1 | | 10/2009 | Kousaka | |
| 2009/0264613 A1 | * | 10/2009 | Kuma | ................... C07C 319/14 528/60 |
| 2010/0029890 A1 | | 2/2010 | Kawato et al. | |
| 2011/0065884 A1 | | 3/2011 | Kawato et al. | |
| 2011/0190466 A1 | | 8/2011 | Hayashi et al. | |

FOREIGN PATENT DOCUMENTS

| | | | |
|---|---|---|---|
| JP | 2541582 B2 | * | 10/1996 |
| KR | 10 2008 0103082 A | | 11/2008 |
| KR | 10 2009 0069297 A | | 6/2009 |
| KR | 10-2010-0119601 A | | 11/2010 |
| WO | WO 2008/026727 A1 | | 3/2008 |

OTHER PUBLICATIONS

JP 2541582 B2 derwent English Abstract Oct. 9, 1996.*
International Search Report (PCT/ISA/210) dated Sep. 28, 2012, by the Korean Patent Office as the International Searching Authority for International Application No. PCT/KR2012/001590.
Fundamental Pharmaceutical Organic Chemistry (2nd Edition) Hirokowa Publishing Company, published Mar. 25, 2005.†
Organic Chemistry Structure and Function by K. Peter. C. Vollhardt and Neil E. Schore (4th Edition), published Sep. 19, 2007.†
Review of Polarography, 1964, vol. 12, No. 4.†

\* cited by examiner
† cited by third party

*Primary Examiner* — Jeffrey Washville
(74) *Attorney, Agent, or Firm* — Susan Paik, Esq.

(57) ABSTRACT

Disclosed is a method of producing a high-quality thiourethane-based optical material using a general-purpose polyisocyanate compound. According to the method, the pH of a polythiol compound is adjusted to 3.1 to 7 to prevent the occurrence of whitening, which is a problem of the prior art arising from the dissolution of a pressure-sensitive adhesive from a pressure-sensitive adhesive tape upon lens casting. The pH adjustment increases the reaction rate of a resin composition including the polythiol compound. The use of the polythiol compound whose pH is adjusted enables the production of a thiourethane-based optical material that does not suffer from whitening at the edges of the optical lens and nonuniformity polymerization. Further disclosed are a resin composition for a thiourethane-based optical material, and an optical material including a resin produced by the method.

10 Claims, No Drawings

US 10,067,266 B2

METHOD OF PRODUCING RESIN FOR THIOURETHANE-BASED OPTICAL MATERIAL USING GENERAL-PURPOSE POLYISOCYANATE COMPOUND, RESIN COMPOSITION FOR THIOURETHANE-BASED OPTICAL MATERIAL AND THIOURETHANE-BASED OPTICAL MATERIAL INCLUDING RESIN PRODUCED BY THE METHOD

TECHNICAL FIELD

The present invention relates to a method of producing an optical material by polymerizing a resin composition including a thiol-containing compound and a compound having isocyanate groups. More particularly, the present invention relates to a method of producing a high-quality thiourethane-based optical material using a general-purpose polyisocyanate compound, a resin composition for a thiourethane-based optical material, and a thiourethane-based optical material including a resin produced by the method.

BACKGROUND ART

Plastic optical materials are lightweight, hardly fragile and tintable compared to inorganic optical materials. Various plastic materials, such as resins, are currently used in optical materials and are gradually required to have better physical properties.

Polythiourethane optical resins produced using polythiol compounds and isocyanate compounds are widely used as optical lens materials due to their excellent optical properties, including high transparency, Abbe number, transmittance and tensile strength. However, optical materials produced by curing resin compositions including polythiol compounds and general-purpose isocyanate compounds suffer from frequent nonuniformity polymerization or whitening, which worsens the optical properties of the optical resins. General-purpose isocyanate compounds and polythiol compounds as main components of resin compositions for thiourethane lenses are prone to nonuniformity polymerization, whitening and clouding depending on their miscibility. In contrast, optical resins produced by heat curing of highly miscible isocyanate compounds and polythiol compounds do not substantially suffer from the problems of nonuniformity polymerization and whitening even when the polythiol compounds are not specially treated. Such isocyanate compounds include, for example, 3,8-bis(isocyanatomethyl)tricyclo[5.2.1.0$^{2.6}$]decane, 3,9-bis(isocyanatomethyl)tricyclo[5.2.1.0$^{2.6}$]decane, 4,8-bis(isocyanatomethyl)tricyclo[5.2.1.0$^{2.6}$]decane, 4,9-bis(isocyanatomethyl)tricyclo[5.2.1.0$^{2.6}$]decane, 2,5-bis(isocyanatomethyl)bicyclo[2.2.1]heptane, and 2,6-bis(isocyanatomethyl)bicyclo[2.2.1]heptanes. However, the isocyanate compounds are difficult to prepare, which incurs considerable preparation costs. As a consequence, the use of the isocyanate compounds inevitably increases the production cost of thiourethane lenses. Meanwhile, optical resins obtained by curing inexpensive general-purpose isocyanates and polythiol compounds suffer from frequent nonuniformity polymerization or whitening. Such isocyanate compounds include, for example, isophorone diisocyanate, dicyclohexylmethane-4,4-diisocyanate ($H_{12}$MDI), and 1,6-hexamethylenediisocyanate. Particularly, tape whitening and bubbling occur in some cases. These phenomena adversely affect the performance of optical materials and are causes of high defective proportion and low lens quality.

DISCLOSURE OF THE INVENTION

Technical Problem

The present invention has been made in an effort to prevent the occurrence of nonuniformity polymerization and whitening when optical materials are produced by polymerization of general-purpose isocyanate compounds, and it is an object of the present invention to provide a high-quality thiourethane-based optical material that does not suffer from the problems of nonuniformity polymerization and whitening despite the use of a general-purpose polyisocyanate compound. In the present invention, an optical material is produced by polymerization of an inexpensive general-purpose isocyanate compound such as isophorone diisocyanate, dicyclohexylmethane-4,4-diisocyanate ($H_{12}$MDI), and 1,6-hexamethylenediisocyanate and a polythiol compound whose pH is adjusted to a predetermined range. The pH adjustment prevents the occurrence of dissolution from a pressure-sensitive adhesive tape and whitening at the edges of the optical lens. Specifically, the present inventors have found that an inorganic acid remaining in a composition after inorganic acid treatment in the production of a polythiol compound deteriorates the activity of a polymerization catalyst for the production of an optical resin, and as a result, the reaction rate is reduced, causing the occurrence of dissolution and whitening phenomena. Based on this finding, the present invention provides a solution to the problems through pH adjustment. In the present invention, despite the use of an inexpensive general-purpose isocyanate compound, increased reactivity by pH adjustment makes the polymerizable composition viscous to prevent the occurrence of dissolution from a pressure-sensitive adhesive tape and whitening at the edges of the optical lens.

Technical Solution

According to an aspect of the present invention, there is provided a method of producing a resin for a thiourethane-based optical material, including (a) adjusting the pH of a polythiol compound to 3.1 to 7, and (b) mixing the polythiol compound having a pH of 3.1 to 7 with a polyisocyanate compound to prepare a resin composition, followed by cast polymerization.

According to another aspect of the present invention, there is provided a resin composition for a thiourethane-based optical material which includes a polythiol compound having a pH of 3.1 to 7 and a polyisocyanate compound.

In the present invention, the pH of the polythiol compound as a main component of the resin composition for an optical lens is adjusted by treatment with a basic substance to control the reaction rate of the resin composition. This pH adjustment prevents the occurrence of whitening, which is a problem of the prior art. Organotin compounds are usually used as catalysts for the production of polythiourethane resins. The use of the catalysts for the production of polythiourethane resins retards the reaction rate, and as a result, pressure-sensitive adhesive tapes are dissolved, leading to the occurrence of whitening. In the present invention intended to solve the problems of the prior art, the pH of the polythiol compound included in the resin composition for an optical lens is adjusted to 3.1 to 7 by treatment with an organic or inorganic basic substance. The pH adjustment increases the reaction rate of the resin composition, making the resin composition viscous. As a result, the solubility of the resin composition is reduced to prevent dissolution from a pressure-sensitive adhesive tape, which is a cause of the occurrence of whitening.

According to the present invention, a polythiourethane optical material with stable quality can be produced using a general-purpose polyisocyanate compound and optionally an organotin compound, which has been used as a catalyst for the production of polythiourethane resins. For the production of a polythiourethane resin, cast polymerization is usually performed in which the optical resin composition is injected into a mold and is cured by heating. The polymerization is allowed to proceed while slowly elevating the temperature from low to high over several to several tens of hours. At this time, it is necessary to finish the polymerization in order to sufficiently draw the characteristics of the resin. To this end, the use of a catalyst strongly active for polymerization or the use of a catalyst in a large amount is considered. However, an increase in the amount of a catalyst for rapid polymerization leads to a high defective proportion of lenses. Meanwhile, the use of a catalyst in a small amount causes a low reaction rate, and as a result, a pressure-sensitive adhesive is dissolved from a tape, resulting in the occurrence of whitening at the edges of lenses.

The present inventors have found that the acidity of metal catalysts affecting the activity of polymerization is a cause of the occurrence of optical deformation or clouding, which impedes the production of resins with stable quality. That is, the present inventors have found that a variation in polymerization rate resulting from different acidities of additives is an impediment to the production of resins with stable quality. Particularly, acidic phosphate-based internal release agents or polythiol compounds used for the production of plastic lens materials for spectacles may have different acidities according to their production lots. Such variation in pH is estimated to be an obstacle to the production of plastic lenses with stable quality. Washing with an inorganic acid is an essential step in the production of a polythiol compound. The inorganic acid remains unremoved after washing to lower the pH of the polythiol compound. The low pH decreases the activity of a catalyst, leading to a reduction in the reaction rate of a curable resin composition including the polythiol compound. This is a cause of high solubility of the curable resin composition. Thus, a pressure-sensitive adhesive is dissolved from a tape and the edges of lenses are whitened. These problems are particularly serious when using general-purpose polyisocyanate compounds, such as isophorone diisocyanate, dicyclohexylmethane-4,4-diisocyanate ($H_{12}MDI$) and hexamethylene diisocyanate, which are poorly miscible with the polythiol. As a result of research in view of the above problems, the present inventors have found that when the pH of a polythiol compound is adjusted to 3.1 to 7 during washing, the reaction rate and the initial viscosity increase to minimize the dissolution of a pressure-sensitive adhesive from a tape, which is a cause of whitening, and at the same time, no nonuniformity polymerization appears. The present invention has been achieved based on this finding.

According to another aspect of the present invention, there is provided a resin for a thiourethane-based optical material which is produced by the method.

According to yet another aspect of the present invention, there is provided an optical lens including the resin. The optical lens is particularly a spectacle lens.

Advantageous Effects

According to the present invention, a polythiourethane-based lens free from clouding can be produced using a polythiol compound whose pH is adjusted to a predetermined range, despite the use of a general-purpose polyisocyanate compound. The pH adjustment increases the reaction rate without the use of a catalyst. In addition, the pH adjustment reduces a variation in polymerization rate resulting from the acidity of the polythiol compound to overcome the problem of nonuniformity polymerization. Furthermore, an inorganic acid, such as hydrochloric acid, remaining in the course of the production of the polythiol compound can be removed, thus avoiding the danger of corrosion of a stainless reactor and a filter. According to the present invention, the pH adjustment can increase the reaction rate while maintaining the characteristics of an organotin catalyst without deteriorating the degree of activity of the catalyst. Therefore, a polythiourethane-based optical material can be produced that does not suffer from whitening as well as nonuniformity polymerization.

DESCRIPTION OF EMBODIMENTS

The present invention is directed to the production of a polythiol compound whose pH is adjusted to a predetermined range, thus being suitable for use in a resin composition for an optical lens. The polythiol compound does not cause whitening and nonuniformity polymerization, which are problems of the prior art.

Whitening is most responsible for high defective proportion of polythiourethane-based resins. Based on the finding that the pH of a polythiol compound as a main component of a polythiourethane-based lens is associated with the reaction rate of the polythiol compound, the present invention is intended to produce a resin free from whitening. The pH of the polythiol compound is adjusted as follows. First, in a production of the polythiol compound, an organic layer usually is washed with an inorganic acid and washed several times with an aqueous basic solution, e.g., water. After the washing, a basic solution is added to the polythiol compound for alkali treatment to adjust the pH to at least 7. Then, the dilute solvent is concentrated and filtered to obtain the polythiol compound having a pH of 3.1 to 7. Alternatively, a basic solution (including a solid) is added to the treated polythiol compound to obtain the polythiol compound having a pH of 3.1 to 7. If the polythiol compound has a pH of 2 to 3, severe whitening occurs. If the polythiol compound has a pH which is equal to or higher than 7, severe nonuniformity polymerization occurs. In contrast, when the polythiol compound has a pH of 3.1 to 7, no whitening and no nonuniformity polymerization occur. More preferably, the polythiol compound has a pH in the range of 3.5 to 6. Within this range, the polythiol compound does not suffer from whitening and nonuniformity polymerization.

There is no restriction on the state of the basic substance used to treat the polythiol. For example, the basic substance may be a gas, liquid, solid or a mixture thereof. Amines, including aqueous ammonia, are particularly suitable. Representative examples of the amines include; monofunctional primary amine compounds, such as ethylamine, n-propylamine, isopropylamine, n-butylamine, sec-butylamine, t-butylamine, pentylamine, hexylamine, heptylamine, octylamine, decylamine, laurylamine, myristylamine, 3-pentylamine, 2-ethylhexylamine, 1,2-dimethylhexylamine, allylamine, aminomethylbicycloheptane, cyclopentylamine, cyclohexylamine, 2,3-dimethylcyclohexylamine, aminomethylcyclohexane, aniline, benzylamine, phenethylamine, 2,3- and 4-methylbenzylamine, o-, m- and p-methylaniline, o-, m- and p-ethylaniline, aminomorpholine, naphthylamine, furfurylamine, α-aminodiphenylmethane, toluidine, aminopyridine, aminophenol, aminoethanol, 1-aminopropanol, 2-aminopropanol, aminobutanol, aminopentanol, aminohexanol, methoxyethylamine, 2-(2-aminoethoxy)ethanol, 3-ethoxypropylamine, 3-propoxypropylamine, 3-butoxypropylamine, 3-isopropoxypropylamine, 3-isobutoxypropylamine, and 2,2-diethoxyethylamine; primary polyamine compounds, such as ethylenediamine, 1,2- and 1,3-diaminopropane, 1,2-, 1,3- and 1,4-diaminobutane, 1,5-diaminopentane, 1,6-diaminohexane, 1,7-diaminoheptane, 1,8-diaminooctane, 1,10-diaminodecane, 1,2-, 1,3- and 1,4-diaminocyclohexane, o-, m- and p-diaminobenzene, 3,4- and 4,4'-diaminobenzophenone, 3,4- and 4,4'-diaminodiphenylether, 4,4'-diaminodiphenylmethane, 4,4'-diaminodiphenylsulfide, 3,3'- and 4,4'-diaminodiphenylsulfone, 2,7-diaminofluorene, 1,5-, 1,8- and 2,3-diaminonaphthalene, 2,3-, 2,6- and 3,4-diaminopyridine, 2,4- and 2,6-diaminotoluene, m- and p-xylylenediamine, isophoronediamine, diaminomethylbicycloheptane, 1,3- and 1,4-diaminomethylcyclohexane, 2- and 4-aminopiperidine, 2- and 4-aminomethylpiperidine, 2- and 4-aminoethylpiperidine, N-aminoethylmorpholine, and N-aminopropylmorpholine; monofunctional secondary amine compounds, such as diethylamine, dipropylamine, di-n-butylamine, di-sec-butylamine, diisobutylamine, di-n-pentylamine, di-3-pentylamine, dihexylamine, dioctylamine, di(2-ethylhexyl)amine, methylhexylamine, diallylamine, N-methylallylamine, piperidine, pyrrolidine, diphenylamine, N-methylamine, N-ethylamine, dibenzylamine, N-methylbenzylamine, N-ethylbenzylamine, dicyclohexylamine, N-methylaniline, N-ethylaniline, dinaphthylamine, 1-methylpiperazine, and morpholine; and secondary and tertiary polyamine compounds, such as N,N'-dimethylethylenediamine, N,N'-dimethyl-1,2-diaminopropane, N,N'-dimethyl-1,3-diaminopropane, N,N'-dimethyl-1,2-diaminobutane, N,N'-dimethyl-1,3-diaminobutane, N,N'-dimethyl-1,4-diaminobutane, N,N'-dimethyl-1,5-diaminopentane, N,N'-dimethyl-1,6-diaminohexane, N,N'-dimethyl-1,7-diaminoheptane, N,N'-diethylethylenediamine, N,N'-diethyl-1,2-diaminopropane, N,N'-diethyl-1,3-diaminopropane, N,N'-diethyl-1,2-diaminobutane, N,N'-diethyl-1,3-diaminobutane, N,N'-diethyl-1,4-diaminobutane, N,N'-diethyl-1,5-diaminopentane, N,N'-diethyl-1,6-diaminohexane, N,N'-diethyl-1,7-diaminoheptane, piperazine, 2-methylpiperazine, 2,5-dimethylpiperazine, 2,6-dimethylpiperazine, homopiperazine, 1,1-di-(4-piperidyl)methane, 1,2-di-(4-piperidyl)ethane, 1,3-di-(4-piperidyl)propane, 1,4-di(4-piperidyl)butane, and tetramethylguanidine. These amines may be used alone or as a mixture of two or more thereof. In addition to these amines, basic solutions, such as aqueous alkaline solutions, may also be used.

As the isocyanate compound reacting with the polythiol compound, there may be used an inexpensive general-purpose polyisocyanate compound, which contributes to a reduction in the production cost of a thiourethane optical material. Particularly, the isocyanate compound is isophorone diisocyanate, dicyclohexylmethane-4,4-diisocyanate hexamethylene diisocyanate, or a mixture thereof.

A mixture of the isocyanate compound with another iso(thio)cyanate compound may also be used. Examples of such iso(thio)cyanate compounds include: aliphatic isocyanate compounds, such as 2,2-dimethylpentane diisocyanate, 2,2,4-trimethylhexane diisocyanate, butene diisocyanate, 1,3-butadiene-1,4-diisocyanate, 2,4,4-trimethylhexamethylene diisocyanate, 1,6,11-undecatriisocyanate, 1,3,6-hexamethylene triisocyanate, 1,8-diisocyanate-4-isocyanatomethyloctane, bis(isocyanatoethyl)carbonate, and bis(isocyanatoethyl)ether; alicyclic isocyanate compounds, such as isophorone diisocyanate, 1,2-bis(isocyanatomethyl)cyclohexane, 1,3-bis(isocyanatomethyl)cyclohexane, 1,4-bis(isocyanatomethyl)cyclohexane, dicyclohexylmethane diisocyanate, cyclohexane diisocyanate, methylcyclohexane diisocyanate, dicyclohexyldimethylmethane isocyanate, and 2,2-dimethyldicyclohexylmethane isocyanate; aromatic isocyanate compounds, such as bis(isocyanatoethyl)benzene, bis(isocyanatopropyl)benzene, bis(isocyanatobutyl)benzene, bis(isocyanatomethyl)naphthalene, bis(isocyanatomethyl)diphenylether, phenylene diisocyanate, ethylphenylene diisocyanate, isopropylphenylene diisocyanate, dimethylphenylene diisocyanate, diethylphenylene diisocyanate, diisopropylphenylene diisocyanate, trimethylbenzene triisocyanate, benzene triisocyanate, biphenyl diisocyanate, toluidine diisocyanate, 4,4-diphenylmethane diisocyanate, 3,3-dimethyldiphenylmethane-4,4-diisocyanate, bibenzyl-4,4-diisocyanate, bis(isocyanatophenyl)ethylene, 3,3-dimethoxybiphenyl-4,4-diisocyanate, hexahydrobenzene diisocyanate, and hexahydrodiphenylmethane-4,4-diisocyanate; sulfur-containing aliphatic isocyanate compounds, such as bis(isocyanatoethyl)sulfide, bis(isocyanatopropyl)sulfide, bis(isocyanatohexyl)sulfide, bis(isocyanatomethyl)sulfone, bis(isocyanatomethyl)disulfide, bis(isocyanatopropyl)disulfide, bis(isocyanatomethylthio)methane, bis(isocyanatoethylthio)methane, bis(isocyanatoethylthio)ethane, bis(isocyanatomethylthio)ethane, and 1,5-diisocyanato-2-isocyanatomethyl-3-thiapentane; sulfur-containing aromatic isocyanate compounds, such as diphenylsulfide-2,4-diisocyanate, diphenylsulfide-4,4-diisocyanate, 3,3-dimethoxy-4,4-diisocyanatodibenzylthioether, bis(4-isocyanatomethylbenzene)sulfide, 4,4-methoxybenzenethioethylene glycol-3,3-diisocyanate, diphenyldisulfide-4,4-diisocyanate, 2,2-dimethyldiphenyldisulfide-5,5-diisocyanate, 3,3-dimethyldiphenyldisulfide-5,5-diisocyanate, 3,3-dimethyldiphenyldisulfide-6,6-diisocyanate, 4,4-dimethyldiphenyldisulfide-5,5-diisocyanate, 3,3-dimethoxy diphenyldisulfide-4,4-diisocyanate, and 4,4-dimethoxydiphenyldisulfide-3,3-diisocyanate; and sulfur-containing heterocyclic isocyanate compounds, such as 2,5-diisocyanatothiophene, 2,5-bis(isocyanatomethyl)thiophene, 2,5-diisocyanatotetrahydrothiophene, 2,5-bis(isocyanatomethyl)tetrahydrothiophene, 3,4-bis(isocyanatomethyl)tetrahydrothiophene, 2,5-diisocyanato-1,4-dithiane, 2,5-bis(isocyanatomethyl)-1,4-dithiane, 4,5-diisocyanato-1,3-dithiolane, 4,5-bis(isocyanatomethyl)-1,3-dithiolane, and 4,5-bis(isocyanatomethyl)-2-methyl-1,3-dithiolane. These iso(thio)cyanate compounds may be used alone or as a mixture of two or more thereof.

The polythiol compound is preferably selected from the group consisting of 4-mercaptomethyl-1,8-dimercapto-3,6-dithiaoctane, 2,3-bis(2-mercaptoethylthio)propane-1-thiol, 2,2-bis(mercaptomethyl)-1,3-propanedithiol, bis(2-mercaptoethyl)sulfide, tetrakis(mercaptomethyl)methane; 2-(2-mercaptoethylthio)propane-1,3-dithiol, 2-(2,3-bis(2-mercaptoethylthio)propylthio)ethanethiol, bis(2,3-dimercaptopropanyl)sulfide, bis(2,3-dimercaptopropanyl)disulfide, 1,2-bis(2-mercaptoethylthio)-3-mercaptopropane, 1,2-bis(2-(2-mercaptoethylthio)-3-mercaptopropylthio)ethane, bis(2-(2-mercaptoethylthio)-3-mercaptopropyl)sulfide, 2-(2-mercaptoethylthio)-3-2-mercapto-3-[3-mercapto-2-(2-mercaptoethylthio)-propylthio]propylthio-propane-1-thiol, 2,2-bis-(3-mercapto-propionyloxymethyl)-butyl ester, 2-(2-mercaptoethylthio)-3-(2-(2-[3-mercapto-2-(2-mercaptoethylthio)-propylthio]ethylthio)ethylthio)propane-1-thiol, (4R, 11S)-4,11-bis(mercaptomethyl)-3,6,9,12-tetrathiatetradecane-1,14-dithiol, (S)-3-((R-2,3- dimercaptopropyl)thio)propane-1,2-dithiol, (4R,14R)-4,14-bis(mercaptomethyl)-3,6,9,12,15-pentathiaheptane-1,17-dithiol, (S)-3-((R-3-mercapto-2-((2-mercaptoethyl)thio)propyl)thio)propyl)thio)-2-((2-mercaptoethyl)thio)propane-1-thiol, 3,3'-dithiobis(propane-1,2-dithiol), (7R,11S)-7,11-bis(mercaptomethyl)-3,6,9,12,15-pentathiaheptadecane-1,17-dithiol, (7R,12S)-7,12-bis(mercaptomethyl)-3,6,9,10,13,16-hexathiaoctadecane-1,18-dithiol, 5,7-dimercaptomethyl-1,1'-dimercapto-3,6,9-trithiaundecane, 4,7-dimercaptomethyl-1,1'-dimercapto-3,6,9-trithiaundecane, 4,8-dimercaptomethyl-1,1'-dimercapto-3,6,9-trithiaundecane, pentaerythritol tetrakis(3-mercaptopropionate), trimethylolpropane tris(3-mercaptopropionate), pentaerythritol tetrakis(2-mercaptoacetate), bispentaerythritol-ether-hexakis(3-mercaptopropionate), 1,1,3,3-tetrakis(mercaptomethylthio)propane, 1,1,2,2-tetrakis(mercaptomethylthio)ethane, 4,6-bis(mercaptomethylthio)-1,3-dithiane, 2-(2,2-bis(mercaptodimethylthio)ethyl)-1,3-dithiethane, and mixtures thereof.

A combination of the polythiol compound treated with the basic substance and one or more polythiol compounds untreated with the basic substance may also be used.

For better optical properties of the polythiourethane optical resin, it is necessary to control the impact resistance and specific gravity of the polythiourethane optical resin and the viscosity of the monomers. To this end, a reactive resin modifier may be added to the resin composition.

An olefin compound may be added as the resin modifier. Examples of such olefin compounds include, but are not limited to; (meth)acrylate compounds, such as benzyl acrylate, benzyl methacrylate, butoxyethyl acrylate, butoxymethyl methacrylate, cyclohexyl acrylate, cyclohexyl methacrylate, 2-hydroxyethyl acrylate, 2-hydroxymethyl methacrylate, glycidyl acrylate, glycidyl methacrylate, phenoxyethyl acrylate, phenoxyethyl methacrylate, phenyl methacrylate, ethylene glycol diacrylate, ethylene glycol dimethacrylate, diethylene glycol diacrylate, diethylene glycol dimethacrylate, triethylene glycol diacrylate, triethylene glycol dimethacrylate, tetraethylene glycol diacrylate, tetraethylene glycol dimethacrylate, polyethylene glycol diacrylate, polyethylene glycol dimethacrylate, neopentyl glycol diacrylate, neopentyl glycol dimethacrylate, ethylene glycol bisglycidyl acrylate, ethylene glycol bisglycidyl methacrylate, bisphenol A diacrylate, bisphenol A dimethacrylate, 2,2-bis(4-acryloxyethoxyphenyl)propane, 2,2-bis(4-methacryloxyethoxyphenyl)propane, 2,2-bis(4-acryloxydiethoxyphenyl)propane, 2,2-bis(4-methacryloxydiethoxyphenyl)propane, bisphenol F diacrylate, bisphenol F dimethacrylate, 1,1-bis(4-acryloxyethoxyphenyl)methane, 1,1-bis(4-methacryloxyethoxyphenyl)methane, 1,1-bis(4-acryloxydiethoxyphenyl)methane, 1,1-bis(4-methacryloxydiethoxyphenyl)methane, dimethylol tricyclodecane diacrylate, trimethylol propane triacrylate, trimethylol propane trimethacrylate, glycerol diacrylate, glycerol dimethacrylate, pentaerythritol triacrylate, pentaerythritol tetraacrylate, pentaerythritol tetramethacrylate, methyl thioacrylate, methyl thiomethacrylate, phenyl thioacrylate, benzyl thiomethacrylate, xylylene dithioldiacrylate, xylylene dithiol dimethacrylate, mercaptoethyl sulfide diacrylate, and mercaptoethyl sulfide dimethacrylate; allyl compounds, such as allyl glycidyl ether, diallyl phthalate, diallyl terephthalate, diallyl isophthalate, diallyl carbonate, and diethylene glycol bisallyl carbonate; vinyl compounds, such as styrene, chlorostyrene, methylstyrene, bromostyrene, dibromostyrene, divinylbenzene, and 3,9-divinylspirobi(m-dioxane). These olefin compounds may be used alone or as a mixture of two or more thereof.

In the present invention, the isocyanate compound and the polythiol compound as raw materials, and the resin modifier may be used in amounts such that the molar ratio of the functional groups (NCO+NCS)/(SH+OH) is typically in the range of 0.5 to 3.0, preferably 0.6 to 2.0, more preferably 0.8 to 1.5.

The resin composition of the present invention may optionally further include one or more additives selected from internal release agents, UV absorbers, dyes, stabilizers, and blowing agents. For example, the resin for a urethane-based optical material may be produced by injecting the resin composition, which includes the polythiol compound, the polyisocyanate compound and optionally the additives, into a mold, and curing the resin composition in the mold. One or more compounds copolymerizable with the urethane resin may be further added to the resin composition. Examples of such copolymerizable compounds include epoxy compounds, thioepoxy compounds, compounds having vinyl or unsaturated groups, and metal compounds.

The isocyanate compound, the polythiol compound and the catalyst and the additives are usually mixed at a temperature not higher than 25° C. to prepare the resin composition for an optical lens. In some cases, a temperature much lower than 25° C. is preferred in view of the pot life of the resin composition. If the catalyst and the additives are not readily soluble in the monomers, they may be dissolved in the isocyanate, the thiol or a mixture of the monomers by pre-heating.

The polythiourethane resin of the present invention is produced by cast polymerization. First, the polymerizable composition according to the present invention is injected into a mold, which is held by a gasket or a tape. In many cases, it is preferred to perform degassing under reduced pressure, filtration under pressure or reduced pressure, etc. depending on physical properties required for a plastic lens to be obtained. The polymerization conditions may greatly vary depending on the polymerizable composition, the kind and amount of the catalyst, the shape of the mold, etc. The polymerization is performed at a temperature of about −50 to 150° C. for 1 to 50 hours, but is not limited to these conditions. The curing is preferably performed for 1 to 48 hours by maintaining the temperature or slowly elevating the temperature in the range of 10 to 150° C.

If needed, the obtained polythiourethane resin may be treated, for example, by annealing. The thermal treatment is usually performed at a temperature of 50 to 150° C., preferably 90 to 140° C., more preferably 100 to 130° C.

The polythiourethane resin of the present invention may be molded into various shapes by changing the mold upon cast polymerization. The molded products can be used in various optical applications, including spectacle lenses, camera lenses, and light emitting diodes (LEDs). The polythiourethane resin of the present invention is particularly suitable for use in optical materials and optical devices, such as spectacle lenses, camera lenses, and light emitting diodes.

Coating layers may be formed on one or both surfaces of a plastic lens using the polythiourethane resin of the present invention. As the coating layers, mention may be made of primer layers, hard coat layers, anti-reflective layers, anti-turbidity coating film layers, anti-fouling layers, and water-repellent layers. These coating layers may be used singly or may be used in combination to form a multilayer structure. When it is intended to form the coating layers on both surfaces of a plastic lens, the coating layers may be the same as or different from each other.

The optical material composed of the urethane-based resin according to the present invention is characterized by less tape whitening or bubbles. In addition, the optical material can be produced in high yield. The optical material of the present invention may be optionally physically or chemically treated, for example, by surface polishing, antistatic treatment, hard coating treatment, anti-reflective coating treatment, dyeing or photochromic treatment, for the purpose of imparting anti-reflection, hardness, wear resistance, chemical resistance, anti-turbidity or fashionability to the optical material. The urethane resin of the present invention has high refractive index indicating low dispersity, is advantageous in terms of heat resistance and durability, and exhibits good impact resistance despite its light weight. The urethane resin is satisfactory in color. Due to these advantages, the urethane resin of the present invention is suitable for use in optical materials, such as lenses and prisms, and can find particular application in lenses, including spectacle lenses and camera lenses.

EXAMPLES

The present invention will be explained in detail with reference to the following examples. However, these examples are given for illustrative purposes only and are not intended to limit the scope of the invention.

Test Methods

Pot life, resin whitening, Nonuniformity polymerization and lens performance (refractive index, Abbe number and heat resistance) were evaluated by the following testing methods.

Change in viscosity was observed at 30° C. using a viscometer (SV-10, A&D Company Limited), and the time required to reach a viscosity of 300 cps was defined as pot life.

Resin whitening was evaluated as resin transparency. The obtained resin was irradiated with a projector in a dark place. The turbidity of a lens and the presence of opaque materials were determined by visual observation. The lens was judged to be 'o' (no whitening) when no turbidity and no opaque materials were observed and judged to be "x" (whitening) when turbidity and opaque materials were observed.

Nonuniformity polymerization (striation) was evaluated by observing whether optical deformation occurred in a lens after the lens was irradiated with a mercury arc lamp (USH-102D, USHIO). The lens was judged to be 'o' (no nonuniformity polymerization when no heterogeneous pattern was observed within a radius of 300 mm from the center of the lens and judged to be 'x' (nonuniformity polymerization) when a heterogeneous pattern was observed within a radius of 30 mm from the center of the lens.

Refractive index (nE) and Abbe number were measured using Abbe refractometers (IT and DR-M4, Atago) at 20° C.

Glass transition temperature (Tg) was determined by measuring TMA with a penetration method (load 20 g, pin tip 0.5 mm Φ, heating rate 5° C./min) (TMAQ400, TA instruments) under high-purity nitrogen.

Synthesis Example 1

532 g of 2-mercaptoethanol and 1,010 g of sodium hydroxide (25% aqueous solution) were mixed to prepare a homogeneous solution, and then 300 g of epichlorohydrin was added dropwise to the solution at 40° C. or below. After completion of the dropwise addition, the mixture was further stirred at 45° C. for 1 hr. The mixture was allowed to cool to room temperature, and 2,040 g of a 35% aqueous hydrochloric acid solution and 926 g of thiourea were added thereto. The mixture was heated with stirring at 108° C. for 4 hr. Thereafter, the resulting mixture was cooled to 30° C. or below, and 2,000 g of a 25% aqueous ammonia solution was added dropwise thereto while maintaining the temperature at 30° C. or below. After completion of the dropwise addition, hydrolysis was performed at an internal temperature of 65° C. for 1 hr. Then, the reaction mixture was extracted to an organic layer with 1,000 g of toluene. The organic layer was washed with 500 mL of a 35% aqueous hydrochloric acid solution, washed once with 1,000 g of water, and alkali-treated with a 0.5% aqueous ammonia solution (1,000 g). The aqueous layer was discarded and the organic layer was concentrated under reduced pressure, affording 760 g of 2,3-bis(2-mercaptoethylthio)propane-1-thiol (GST) having pH 4.0.

Synthesis Example 2

532 g of 2-mercaptoethanol and 1,010 g of sodium hydroxide (25% aqueous solution) were mixed to prepare a homogeneous solution, and then 300 g of epichlorohydrin was added dropwise to the solution at 40° C. or below. After completion of the dropwise addition, the mixture was further stirred at 45° C. for 1 hr. The mixture was allowed to cool to room temperature, and 2,040 g of a 35% aqueous hydrochloric acid solution and 926 g of thiourea were added thereto. The mixture was heated with stirring at 108° C. for 4 hr. Thereafter, the resulting mixture was cooled to 30° C. or below, and 2,000 g of a 25% aqueous ammonia solution was added dropwise thereto while maintaining the temperature at 30° C. or below. After completion of the dropwise addition, hydrolysis was performed at an internal temperature of 65° C. for 1 hr. Then, the reaction mixture was extracted to an organic layer with 1,000 g of toluene. The organic layer was washed with 500 mL of a 35% aqueous hydrochloric acid solution and washed once with 1,000 g of water. The aqueous layer was discarded. The organic layer was concentrated under reduced pressure and aqueous ammonia was added thereto, affording 763 g of 2,3-bis(2-mercaptoethylthio)propane-1-thiol (GST) having pH 4.5.

Synthesis Example 3

560 g of epichlorohydrin was slowly added dropwise to a mixture of 295 g of ethanedithiol and 10 mL of triethylamine at a reaction temperature set to 40° C. while maintaining the temperature at 45° C. After completion of the dropwise addition, stirring was continued for 1 hr. To the solution was slowly added dropwise a homogeneous solution of 473 g of 2-mercaptoethanol and 968 g of a 25% aqueous NaOH solution while maintaining the temperature at 45° C. After completion of the dropwise addition, the mixture was further stirred at 45° C. for 1 hr. The mixture was allowed to cool to room temperature, and 1,577 g of a 35% aqueous hydrochloric acid solution and 1,013 g of thiourea were added thereto. The mixture was heated with stirring at 108° C. for 4 hr. Thereafter, the resulting mixture was cooled to 30° C. or below, and 1,500 g of a 25% aqueous ammonia solution was added dropwise thereto while maintaining the temperature at 30° C. or below. After completion of the dropwise addition, hydrolysis was performed at an internal temperature of 65° C. for 1 hr. Then, the reaction mixture was extracted to an organic layer with 1,000 g of toluene. The organic layer was washed with 500 mL of a 35% aqueous hydrochloric acid solution and washed once with 1,000 g of water. The aqueous layer was discarded. The organic layer was concentrated under reduced pressure and aqueous ammonia was added thereto, affording 1,203 g of 1,2-bis(2-(2-mercaptoethylthio)-3-mercaptopropylthio)ethane (ETS-4) having pH 5.0.

Synthesis Comparative Example 1

532 g of 2-mercaptoethanol and 1,010 g of sodium hydroxide (25% aqueous solution) were mixed to prepare a homogeneous solution, and then 300 g of epichlorohydrin was added dropwise to the solution at 40° C. or below. After completion of the dropwise addition, the mixture was further stirred at 45° C. for 1 hr. The mixture was allowed to cool to room temperature, and 2,040 g of a 35% aqueous hydrochloric acid solution and 926 g of thiourea were added thereto. The mixture was heated with stirring at 108° C. for 4 hr. Thereafter, the resulting mixture was cooled to 30° C. or below, and 2,000 g of a 25% aqueous ammonia solution was added dropwise thereto while maintaining the temperature at 30° C. or below. After completion of the dropwise addition, hydrolysis was performed at an internal temperature of 65° C. for 1 hr. Then, the reaction mixture was extracted to an organic layer with 1,000 g of toluene. The organic layer was washed with 500 mL of a 35% aqueous hydrochloric acid solution and washed once with 1,000 g of water. The aqueous layer was discarded and the organic layer was concentrated under reduced pressure, affording 755 g of 2,3-bis(2-mercaptoethylthio)propane-1-thiol (GST) having pH 2.8.

Synthesis Comparative Example 2

532 g of 2-mercaptoethanol and 1,010 g of sodium hydroxide (25% aqueous solution) were mixed to prepare a homogeneous solution, and then 300 g of epichlorohydrin was added dropwise to the solution at 40° C. or below. After completion of the dropwise addition, the mixture was further stirred at 45° C. for 1 hr. The mixture was allowed to cool to room temperature, and 2,040 g of a 35% aqueous hydrochloric acid solution and 926 g of thiourea were added thereto. The mixture was heated with stirring at 108° C. for 4 hr. Thereafter, the resulting mixture was cooled to 30° C. or below, and 2,000 g of a 25% aqueous ammonia solution was added dropwise thereto while maintaining the temperature at 30° C. or below. After completion of the dropwise addition, hydrolysis was performed at an internal temperature of 65° C. for 1 hr. Then, the reaction mixture was extracted to an organic layer with 1,000 g of toluene. The organic layer was washed with 500 mL of a 35% aqueous hydrochloric acid solution and washed once with 1,000 g of water. The aqueous layer was discarded. The organic layer was concentrated under reduced pressure and aqueous ammonia was added thereto, affording 769 g of 2,3-bis(2-mercaptoethylthio)propane-1-thiol (GST) having pH 7.5.

Example 1

56 g of isophorone diisocyanate, 44 g of the 2,3-bis(2-mercaptoethylthio)propane-1-thiol (GST) having pH 4.0, 0.1 g of dibutyltin dichloride, HTAQ (20 ppm) and PRD (10 ppm) as organic dyes, 1.5 g of HOPBT as a UV absorber, and 0.1 g of an internal release agent (Zelec UN, STEPAN) were homogenized and dissolved at 20° C. The homogeneous solution was degassed at 400 Pa for 1 hr, filtered through a 1 μm PTFE filter, and injected into a mold consisting of a glass mold and a tape. The mold was placed in a polymerization oven and gradually heated from 25° C. to 130° C. for 21 hr, and was polymerized. After the polymerization was finished, the mold was taken out of the oven. The releasability of the resin from the mold was good. The obtained resin was annealed at 130° C. for 4 hr. The physical properties of the obtained resin have a refractive index (nE) of 1.601, an Abbe number of 39, and a heat resistance (Tg) of 116° C. The state of the solution before injection into the mold was determined by visual observation. As a result of confirming the presence of impurities after demolding, no abnormalities were observed. No whitening was seen and the resin was found to have stable quality. The results of evaluation are shown in Table 1.

Examples 2-6

In the same manner as in Example 1, compositions were prepared as shown in Table 1 and were used to produce lenses. The results of evaluation are shown in Table 1.

Comparative Example 1

56 g of isophorone diisocyanate, 44 g of the 2,3-bis(2-mercaptoethylthio)propane-1-thiol (GST) having pH 2.8, 0.1 g of dibutyltin dichloride, HTAQ (20 ppm) and PRD (10 ppm) as organic dyes, 1.5 g of HOPBT as a UV absorber, and 0.1 g of an internal release agent (Zelec UN, STEPAN) were homogenized and dissolved at 20° C. The homogeneous solution was degassed at 400 Pa for 1 hr, filtered through a 1 μm PTFE filter, and injected into a mold consisting of a glass mold and a tape. The mold was placed in a polymerization oven and gradually heated from 25° C. to 130° C. for 21 hr, and was polymerized. After the polymerization was finished, the mold was taken out of the oven. The releasability of the resin from the mold was good. The resin was annealed at 130° C. for 4 hr. The physical properties of the obtained resin have a refractive index (nE) of 1.602, an Abbe number of 39, and a heat resistance (Tg) of 116° C. The state of the solution before injection into the mold was determined by visual observation. As a result of confirming the presence of impurities after demolding, no abnormalities were observed but severe whitening was seen. The results of evaluation are shown in Table 1.

Comparative Example 2

In the same manner as in Comparative Example 1, compositions were prepared as shown in Table 1 and were used to produce lenses. The results of evaluation are shown in Table 1.

TABLE 1

|  |  | Example No. |  |  |  |  |  | Comparative Example No. |  |
|---|---|---|---|---|---|---|---|---|---|
|  |  | 1 | 2 | 3 | 4 | 5 | 6 | 1 | 2 |
| Monomer composition (g) | GST (pH 4.0) | 44.00 |  | 47.04 |  |  |  |  |  |
|  | GST (pH 4.5) |  |  |  | 48.45 |  | 44.00 |  |  |

TABLE 1-continued

|  |  | Example No. | | | | | | Comparative Example No. | |
| --- | --- | --- | --- | --- | --- | --- | --- | --- | --- |
|  |  | 1 | 2 | 3 | 4 | 5 | 6 | 1 | 2 |
|  | ETS-4 (pH 5.0) |  | 48.90 |  |  | 52.09 |  |  |  |
|  | GST (pH 2.8) |  |  |  |  |  |  | 44.00 |  |
|  | GST (pH 7.5) |  |  |  |  |  |  |  | 44.00 |
|  | IPDI | 56.00 | 51.10 | 30.15 | 18.63 | 27.28 | 56.00 | 56.00 | 56.00 |
|  | HDI |  |  | 22.81 | 32.90 | 20.64 |  |  |  |
| Release agent (g) | Zelec UN | 0.1 | 0.1 | 0.1 | 0.1 | 0.1 | 0.1 | 0.1 | 0.1 |
| UV absorber (g) | HOPBT | 1.5 | 1.5 | 1.5 | 1.5 | 1.5 | 1.5 | 1.5 | 1.5 |
| Polymerization initiator (g) | BTC | 0.1 | 0.1 | 0.1 | 0.1 | 0.1 | 0.1 | 0.1 | 0.1 |
| Organic dyes (ppm) | HTAQ | 20 | 20 | 20 | 20 | 20 | 20 | 20 | 20 |
|  | PRD | 10 | 10 | 10 | 10 | 10 | 10 | 10 | 10 |
| Physical properties of lenses | Refractive index (nE, 20° C.) | 1.601 | 1.611 | 1.608 | 1.609 | 1.614 | 1.601 | 1.60 | 1.601 |
|  | Abbe number | 39 | 38 | 38 | 38 | 38 | 38 | 38 | 38 |
|  | Glass transition temp. (Tg, ° C.) | 116 | 115 | 97 | 82 | 96 | 116 | 116 | 116 |
|  | Nonuniformity polymerization | ○ | ○ | ○ | ○ | ○ | ○ | ○ | x |
|  | Whitening | ○ | ○ | ○ | ○ | ○ | ○ | x | ○ |

As can be seen from the results in Table 1, the use of the polythiol compounds of the present invention (pH 3.1 to 7) treated with aqueous ammonia as the basic solution or to which the basic solution was added could prevent the occurrence of whitening, which is a problem encountered in the use of the polythiol compound having pH 2.8 and the organotin compound as a catalyst. In addition, the polythiol compounds were highly miscible with the isocyanates and could be used to produce polythiourethane resins suitable for use as transparent resins for optical lenses. Particularly, the polythiol compounds were highly miscible with the isocyanates, underwent small variations in polymerization rate, and could be used to produce optical lenses without substantial whitening. If the pH values of the polythiol compounds of Examples 1 and 2 had not been adjusted with the organic or inorganic basic solution, such as alkali hydroxide or amine (including solid and gas), the polythiol compounds were slowly polymerized and had long pot lives. However, the pH adjustment of the thiol compounds by treatment with the basic solution improved the miscibility of the polythiol compounds with the isocyanates, increased the polymerization rates of the polythiol compounds to some extent, and could solve the problems of whitening and nonuniformity polymerization. These results lead to the conclusion that the polythiol compounds whose pH values were adjusted with the basic solution are highly miscible and are suitable for use in the production of polythiourethane resins with stable quality.

ABBREVIATIONS

Monomers
IPDI: Isophorone diisocyanate
HDI: Hexamethylene-1,6-diisocyanate
GST: 2,3-Bis(2-mercaptoethylthio)propane-1-thiol
ETS-4: 1,2-Bis(2-(2-mercaptoethylthio)-3-mercaptopropylthio)ethane
Release Agent ZELEC UN: Phosphate compound (ZELEC UN™, Stepan)
UV Absorber
HOPBT: 2-(2'-hydroxy-5'-t-octylphenyl)benzotriazole
Organic Dyes
HTAQ: 1-Hydroxy-4-(p-toluidin)anthraquinone
PRD: Perinone dye
Polymerization Initiator
BTC: Dibutyltin dichloride

The invention claimed is:

1. A method of producing a resin for a thiourethane-based optical material, the method comprising:
   (a) adjusting the pH of a polythiol compound obtained as an organic layer in a production process through acid washing and water washing, to obtain a polythiol compound having a pH of 3.1 to 7, wherein the step of adjusting the pH of a polythiol compound obtained through acid washing and water washing comprises adding a basic substance to the washed organic layer, followed by concentration and filtration to obtain the polythiol compound having a pH of 3.1 to 7, and
   (b) preparing a resin composition comprising the polythiol compound having the pH of 3.1 to 7 obtained in the step (a), a polyisocyanate compound and an organotin compound as a catalyst and cast polymerizing the composition, wherein the polyisocyanate compound is at least one kind selected from the group consisting of isophorone diisocyanate, dicyclohexylmethane-4,4-diisocyanate ($H_{12}MDI$), hexamethylene diisocyanate, and mixtures thereof,
   and wherein the polythiol compound is selected from the group consisting of 4-mercaptomethyl-1, 8-dimercapto-3,6-dithiaoctane, bis(2-mercaptoethyl) sulfide, bis(2-(2-mercaptoethylthio)-3-mercaptopropyl) sulfide, and mixtures thereof.

2. The method according to claim 1, wherein the pH of the polythiol compound is adjusted to 3.1 to 7 by the addition of an organic or inorganic basic substance.

3. The method according to claim 2, wherein the organic or inorganic basic substance is ammonia, ammonia gas, a primary amine, a secondary amine, a tertiary amine, a quaternary amine, a polyamine, an aqueous alkaline solution, or a mixture thereof.

4. The method according to claim 2, wherein the organic or inorganic basic substance is selected from the group consisting of: monofunctional primary amine compounds, including ammonia, ammonia gas, ethylamine, n-propylamine, isopropylamine, n-butylamine, sec-butylamine, t-butylamine, pentylamine, hexylamine, heptylamine, octylamine, decylamine, laurylamine, myristylamine, 3-pentylamine, 2-ethylhexylamine, 1,2-dimethylhexylamine, allylamine, aminomethylbicycloheptane, cyclopentylamine, cyclohexylamine, 2,3-dimethylcyclohexylamine, aminomethylcyclohexane, aniline, benzylamine, phenethylamine, 2,3- and 4-methylbenzylamine, o-, m- and p-methylaniline, o-, m- and p-ethylaniline, aminomorpholine, naphthylamine, furfurylamine, α-aminodiphenylmethane, toluidine, aminopyridine, aminophenol, aminoethanol, 1-aminopropanol, 2-aminopropanol, aminobutanol, aminopentanol, aminohexanol, methoxyethylamine, 2-(aminoethoxy) ethanol, 3-ethoxypropylamine, 3-propoxypropylamine, 3-butoxypropylamine, 3-isopropoxypropylamine, 3-isobutoxypropylamine, and 2,2-diethoxyethylamine; primary polyamine compounds, including ethylenediamine, 1,2- and 1,3-diaminopropane, 1,2-, 1,3- and 1,4-diaminobutane, 1,5-diaminopentane, 1,6-diaminohexane, 1,7-diaminoheptane, 1,8-diaminooctane, 1,10-diaminodecane, 1,2-, 1,3- and 1,4-diaminocyclohexane, o-, m- and p-diaminobenzene, 3,4- and 4,4'-diaminobenzophenone, 3,4- and 4,4'-diaminodiphenylether, 4,4'-diaminodiphenylmethane, 4,4'-diaminodiphenylsulfide, 3,3'- and 4,4'-diaminodiphenylsulfone, 2,7-diaminofluorene, 1,5-, 1,8- and 2,3-diaminonaphthalene, 2,3-, 2,6- and 3,4-diaminopyridine, 2,4- and 2,6-diaminotoluene, m- and p-xylylenediamine, isophoronediamine, diaminomethylbicycloheptane, 1,3- and 1,4-diaminomethylcyclohexane, 2- and 4-aminopiperidine, 2- and 4-aminomethylpiperidine, 2- and 4-aminoethylpiperidine, N-aminoethylmorpholine, and N-aminopropylmorpholine; monofunctional secondary amine compounds, including diethylamine, dipropylamine, di-n-butylamine, di-sec-butylamine, diisobutylamine, di-n-pentylamine, di-3-pentylamine, dihexylamine, dioctylamine, di(2-ethylhexyl) amine, methylhexylamine, diallylamine, N-methylallylamine, piperidine, pyrrolidine, diphenylamine, N-methylamine, N-ethylamine, dibenzylamine, N-methylbenzylamine, N-ethylbenzylamine, dicyclohexylamine, N-methylaniline, N-ethylaniline, dinaphthylamine, 1-methylpiperazine, and morpholine; secondary and tertiary polyamine compounds, including N,N'-dimethylethylenediamine, N,N'-dimethyl-1,2-diaminopropane, N,N'-dimethyl-1,3-diaminopropane, N,N'-dimethyl-1,2 diaminobutane, N,N'-dimethyl-1,3-diaminobutane, N,N'-dimethyl-1,4-diaminobutane, N,N'-dimethyl-1,5-diaminopentane, N,N'-dimethyl-1,6-diaminohexane, N,N'-dimethyl-1,7-diaminoheptane, N,N'-diethylethylenediamine, N,N'-diethyl-1,2-diaminopropane, N,N'-diethyl-1,3-diaminopropane, N,N'-diethyl-1,2-diaminobutane, N,N'-diethyl-1,3-diaminobutane, N,N'-diethyl-1,4-diaminobutane, N,N'-diethyl-1,5-diaminopentane, N,N'-diethyl-1,6-diaminohexane, N,N'-diethyl-1,7-diaminoheptane, piperazine, 2-methylpiperazine, 2,5-dimethylpiperazine, 2,6-dimethylpiperazine, homopiperazine, 1,1-di-(4-piperidyl) methane, 1,2-di-(4-piperidyl)ethane, 1,3-di-(4-piperidyl) propane, 1, 4-di (4-piperidyl) butane, and tetramethylguanidine; and aqueous alkaline solution; and mixtures thereof.

5. The method according to claim 1, wherein the resin composition further comprises at least one iso(thio)cyanate compounds selected from the group consisting of: aliphatic isocyanate compounds, including 2,2-dimethylpentane diisocyanate, 2,2,4-trimethylhexane diisocyanate, butane diisocyanate, 1,3-butadiene-1,4-diisocyanate, 2,4,4-trimethylhexamethylene diisocyanate, 1,6,11-undecatriisocyanate, 1,3,6-hexamethylene triisocyanate, 1,8-diisocyanate-4-isocyanatomethyloctane, bis(isocyanatoethyl)carbonate, and bis(isocyanatoethyl)ether; alicyclic isocyanate compounds, including, 1,2-bis(isocyanatomethyl)cyclohexane, 1,3-bis(isocyanatomethyl)cyclohexane, 1,4-bis(isocyanatomethyl)cyclohexane, cyclohexane diisocyanate, methylcyclohexane diisocyanate, dicyclohexyldimethylmethane isocyanate, and 2,2-dimethyldicyclohexylmethane isocyanate; aromatic isocyanate compounds, including, bis(isocyanatobutyl)benzene, bis(isocyanatomethyl)naphthalene, bis(isocyanatomethyl)diphenylether, phenylene diisocyanate, ethylphenylene diisocyanate, isopropylphenylene diisocyanate, dimethylphenylene diisocyanate, diethylphenylene diisocyanate, diisopropylphenylene diisocyanate, trimethylbenzene triisocyanate, benzene triisocyanate, biphenyl diisocyanate, toluidine diisocyanate, 4,4-diphenylmethane diisocyanate, 3,3-dimethyldiphenylmethane-4,4-diisocyanate, bibenzyl-4,4-diisocyanate, bis (isocyanatophenyl) ethylene, 3,3-dimethoxybiphenyl-4,4-diisocyanate, hexahydrobenzene diisocyanate, and hexahydrodiphenylmethane-4,4-diisocyanate; sulfur-containing aliphatic isocyanate compounds, including bis(isocyanatoethyl) sulfide, bis(isocyanatopropyl) sulfide, bis(isocyanatohexyl) sulfide, bis(isocyanatomethyl)sulfone, bis(isocyanatomethyl)disulfide, bis(isocyanatopropyl)disulfide, bis(isocyanatomethylthio) methane, bis(isocyanatoethylthio)methane, bis (isocyanatoethylthio) ethane, bis(isocyanatomethylthio)ethane, and 1,5-diisocyanato-2-isocyanatomethyl-3-thiapentane; sulfur-containing aromatic isocyanate compounds, including diphenylsulfide-2,4-diisocyanate, diphenylsulfide-4,4-diisocyanate, 3,3-dimethoxy-4,4-diisocyanatodibenzylthioether, bis(4-isocyanatomethylbenzene)sulfide, 4,4-methoxybenzenethioethylene glycol-3,3-diisocyanate, diphenyldisulfide-4,4-diisocyanate, 2,2-dimethyldiphenyldisulfide-5,5-diisocyanate, 3,3-dimethyldiphenyldisulfide-5,5-diisocyanate, 3,3-dimethyldiphenyldisulfide-6,6-diisocyanate, 4,4-dimethyldiphenyldisulfide-5,5-diisocyanate, 3,3-dimethoxy diphenyldisulfide-4,4-diisocyanate, and 4,4-dimethoxydiphenyldisulfide-3,3-diisocyanate; and sulfur-containing heterocyclic isocyanate compounds, including 2,5-diisocyanatothiophene, 2,5-bis(isocyanatomethyl)thiophene, 2,5-diisocyanatotetrahydrothiophene, 2,5-bis(isocyanatomethyl)tetrahydrothiophene, 3,4-bis(isocyanatomethyl)tetrahydrothiophene, 2,5-diisocyanato1,4-dithiane, 2,5-bis(isocyanatomethyl)-1,4-dithiane, 4,5-diisocyanato-1,3-dithiolane, 4,5-bis(isocyanatomethyl)-1,3-dithiolane, and 4,5-bis(isocyanatomethyl)-2-methyl-1,3-dithiolane.

6. A resin composition for a thiourethane-based optical material produced by the method according to claim 1, comprising a polythiol compound having a pH of 3.1 to 7 and a polyisocyanate compound.

7. A resin for a thiourethane-based optical material produced by the method according to claim 1.

8. An optical lens for a thiourethane-based optical material comprising the resin according to claim 7.

9. The optical lens according to claim 8, wherein the optical lens is a spectacle lens.

10. A method of producing a resin for a thiourethane-based optical material, the method comprising:
(a) adjusting the pH of a polythiol compound, obtained as an organic layer in a production process through acid washing and water washing, to obtain a polythiol compound having a pH of 3.1 to 7, wherein the step of adjusting the pH of a polythiol compound obtained through acid washing and water washing, comprises concentrating and filtering the washed organic layer followed by the addition of a basic substance thereto to obtain a polythiol compound having a pH of 3.1 to 7, and (b) preparing a resin composition comprising the polythiol compound having the pH of 3.1 to 7 obtained in the step (a), a polyisocyanate compound and an organotin compound as a catalyst and cast polymerizing the composition, wherein the polyisocyanate compound is at least one kind selected from the group consisting of isophorone diisocyanate, dicyclohexylmethane-4,4-diisocyanate ($H_{12}MDI$), hexamethylene diisocyanate, and mixtures thereof, and wherein the polythiol compound is selected from the group consisting of 4-mercaptomethyl-1, 8-dimercapto-3,6-dithiaoctane, bis(2-mercaptoethyl) sulfide, bis(2-(2-mercaptoethylthio)-3-mercaptopropyl) sulfide, and mixtures thereof.

* * * * *